United States Patent [19]

Irikura

[11] 4,041,038
[45] Aug. 9, 1977

[54] 1-(3-PHENYLPROPYL)-4-(BETA-ALKOXYA-CRYLOYL)PIPERAZINE DERIVATIVES

[75] Inventor: Tsutomu Irikura, Tokyo, Japan

[73] Assignee: Kyorin Pharmaceutical Co., Ltd., Tokyo, Japan

[21] Appl. No.: 657,278

[22] Filed: Feb. 11, 1976

[30] Foreign Application Priority Data

Dec. 26, 1975 Japan .................................. 50-155133
May 27, 1975 Japan .................................. 50-62551

[51] Int. Cl.$^2$ .................. C07D 295/10; C07D 241/06
[52] U.S. Cl. .................................. 260/268 C; 424/250
[58] Field of Search .................................. 260/268 C

[56] References Cited

PUBLICATIONS

Prasad et al., J. Med. Chemistry, pp. 1144–1150, (1968).

Primary Examiner—Donald G. Daus
Assistant Examiner—Jose Tovar
Attorney, Agent, or Firm—Armstrong, Nikaido & Marmelstein

[57] ABSTRACT

The present invention relates to novel compounds of piperazine derivatives, which are useful as anesthetics, and to processes for producing the same.

19 Claims, No Drawings

1-(3-PHENYLPROPYL)-4-(BETA-ALKOXYA-CRYLOYL)PIPERAZINE DERIVATIVES

DETAILED DESCRIPTION OF THIS INVENTION

The present invention relates to novel derivatives of 1-(3-phenylpropyl)-4-($\beta$-alkoxyacryloyl)piperazine and acid addition salts thereof, as well as to processes for their preparation.

More particularly, the present invention relates to compounds having the general formula [I]

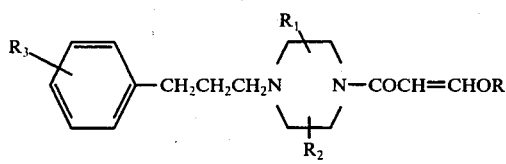

[wherein $R_1$ and $R_2$ represent hydrogen atom or lower alkyl group ($R_1$ and $R_2$ often represent the same alkyl group but not hydrogen atom at the same time), $R_3$ represents hydrogen atom or lower alkyl group, R represents lower alkyl group], and acid addition salts thereof, and to processes for producing the same.

The term "lower alkyl group" includes straight and branched chain groups containing from one to six carbon atoms such as methyl, ethyl, propyl, isopropyl, butyl, isobutyl group.

According to the present invention, the useful compounds can be prepared as follows. Namely, piperazine derivative [II] may be reacted with acrylic acid derivative [III] to provide a compound of the general formula [I] [wherein R, $R_1$, $R_2$ and $R_3$ have the same meanings given above].

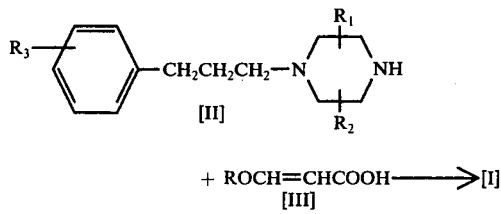

+ ROCH=CHCOOH ⟶ [I]
[III]

Of the derivatives of $\beta$-alkoxyacrylic acid, the acid chloride is the most effective for the purpose. As solvents which are suitable for the reaction may be named benzene, toluene, chloroform, dichloromethane, diethyl ether. As dehydrohalogenating agents may be named triethylamine, pyridine, sodium carbonate, potassium carbonate, sodium hydroxide, potassium hydroxide, though the reaction proceeds in the absence of dehydrohalogenating agent. The reaction can be carried out at various temperatures and preferably at 0°–50° C.

The acid addition salts of [I] can be prepared by the reaction with non-toxic mineral or organic acids.

A compound of [I] has nothing less than one asymmetric carbon, therefore, general formula [I] contains optical isomers. Moreover, general formula [I] contains all stereoisomers which are derived from combination of two asymmetric carbon atoms, if any.

The compounds included in this invention are useful as general anesthetics. The compound of Example 1 (KA-100), for instance, shows a good anesthetic effect in mice, rats and rabbits. The comparisons between 50% anesthetic dose and 50% lethal dose in mice and rats are given in the following table.

| Animals | Drugs | $AD_{50}$* (mg/kg, i.v.) | $LD_{50}$** (mg/kg, i.v.) | $\frac{LD_{50}}{AD_{50}}$ |
|---|---|---|---|---|
| mouse | KA-100 | 7.6 | 37.3 | 4.9 |
| mouse | Thiopental-Na | 20.9 | 90.9 | 4.3 |
| rat | KA-100 | 4.8 | 60.25 | 12.6 |
| rat | Thiopental-Na | 10.7 | 80.3 | 7.5 |

*50% anesthetic dose;
**50% lethal dose

In rabbits, KA-100 caused an anesthesia at the doses of more than 10 mg/kg (i.v.), and the sleeping times at 20 and 30 mg/kg were 20 min. and more than 20 min. respectively.

Thiopental-Na caused an anesthesia lasted for 13 min. after injection of 20 mg/kg and 30 min. after 30 mg/kg. The recovery of rabbits from ataxic state in post-anesthetic period was far more rapid after treatment with KA-100 as compared with thiopental-Na, although pharmacological potencies of both drugs were practically equal. When rabbits were anesthetized with more than 20 mg/kg of KA-100, they lost the withdrawal reflex against nociceptive stimuli (pinching of hind leg toes by a forceps or small incision of abdomen) and against extension of hind legs. These results suggest that KA-100 has anti-nociceptive and muscular relaxant activity. On the other hand, thiopental-Na caused no anti-nociceptive effect and induced muscular rigidity of the same doses with KA-100 in rabbits.

The maleate of KA-100 is soluble in water at nearly physiological pH (pH 6), and does not disturb blood vessels. KA-100 is a novel useful general anesthetic agent with desirable analgesic and muscular relaxant effects, being different from so far widely used intravenous general anesthetics.

The preparation of these compounds is described in the following examples. It is to be understood, however, that the examples are illustrative of the compounds included by this invention and methods for their preparation and are not to be construed as limiting the invention to the particular compounds or methods specifically described.

EXAMPLE 1

Synthesis of trans-1-(3-phenylpropyl)-2,5-dimethyl-4-($\beta$-ethoxyacryloyl)piperazine maleate To a solution of trans-1-(3-phenylpropyl)-2,5-dimethyl-piperazine (56g) in benzene (1l) was added dropwise $\beta$-ethoxyacryloyl chloride (37g), and the reaction mixture was stirred at room temperature for 30 min., and was added an aqueous solution of potassium carbonate. After stirring for 30 min., benzene layer was separated, washed with water, dried, and concentrated to give oily product. An ethyl acetate solution of the oily product was added to a solution of maleic acid (14.6g) in ethyl acetate, and crystals separated gradually, which were recrystallized from ethyl acetate to give 92g (yield 86%) of colorless needles, melting point 110°–112° C.

Analysis, Calcd for $C_{24}H_{34}N_2O_6$: C, 64.55; H, 7.68; N, 6.27. Found : C, 64.63; H, 7.78; N, 6.12.

EXAMPLE 2

Synthesis of trans-1-(3-phenylpropyl)-2,3-dimethyl-4-(β-ethoxyacryloyl)piperazine To a solution of trans-1-(3-phenylpropyl)-2,3-dimethyl-piperazine (2.3g) in 100 ml of benzene was added dropwise β-ethoxyacryloyl chloride (2g), and the reaction mixture was stirred for 30 min., and was added an aqueous solution of potassium carbonate. After stirring for 30 min., benzene layer was separated, washed with water, dried, and evaporated. The residue was purified by column chromatography to give 3g (yield 90% of oily product.

Analysis, Calcd for $C_{20}H_{30}N_2O_2$: C, 72.69; H, 9.15; N, 8.48. Found : C, 72.43; H, 9.38; N, 8.26.

The novel compounds of example 3 to 19 prepared by the methods of Example 1 and 2 are shown in the Table.

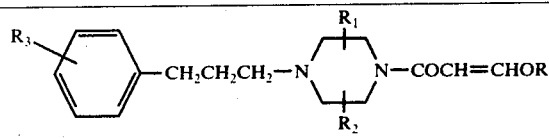

| No. of Example | Substituent R₁ | R₂ | R₃ | R | Molecular formula | M.P. °C | Analysis C% | H% | Calcd Found N% |
|---|---|---|---|---|---|---|---|---|---|
| 3* | 2-CH₃ | 5-CH₃ | m-CH₃ | C₂H₅ | C₂₅H₃₆N₂O₆ | 118–120 | 65.19 / 64.87 | 7.88 / 7.96 | 6.08 / 6.00 |
| 4* | 2-CH₃ | 5-CH₃ | p-CH₃ | C₂H₅ | C₂₅H₃₆N₂O₆ | 126–129 | 65.19 / 64.88 | 7.88 / 7.96 | 6.08 / 5.95 |
| 5 | 3-CH₃ | H | H | C₂H₅ | C₂₃H₃₂N₂O₆ | 131–133 | 63.87 / 63.89 | 7.46 / 7.62 | 6.48 / 6.20 |
| 6** | 3-CH₃ | 5-CH₃ | H | C₂H₅ | C₂₄H₃₄N₂O₆ | 155–157 | 64.55 / 64.35 | 7.68 / 7.83 | 6.27 / 5.99 |
| 7 | 3-C₂H₅ | H | H | C₂H₅ | C₂₄H₃₄N₂O₆ | 121–123 | 64.55 / 64.53 | 7.68 / 7.80 | 6.27 / 6.12 |
| 8 | 3-CH₃ | H | p-CH₃ | C₂H₅ | C₂₄H₃₄N₂O₆ | 132–133 | 64.55 / 64.51 | 7.68 / 7.76 | 6.27 / 6.10 |
| 9* | 2-CH₃ | 5-CH₃ | H | C₂H₅ | C₂₀H₃₀N₂O₂ | oil | 72.69 / 72.50 | 9.15 / 9.40 | 8.48 / 8.35 |
| 10** | 2-CH₃ | 3-CH₃ | H | C₂H₅ | C₂₄H₃₄N₂O₆ | 155–157 | 64.55 / 64.38 | 7.68 / 7.68 | 6.27 / 6.01 |
| 11** | 3-CH₃ | 5-CH₃ | H | CH₃ | C₂₃H₃₂N₂O₆ | 168–169 | 63.87 / 63.71 | 7.46 / 7.58 | 6.48 / 6.35 |
| 12* | 2-CH₃ | 5-CH₃ | H | CH₃ | C₂₃H₃₂N₂O₆ | 133–134 | 63.87 / 63.60 | 7.46 / 7.60 | 6.48 / 6.23 |
| 13* | 2-CH₃ | 3-CH₃ | H | CH₃ | C₁₉H₂₈N₂O₂ | oil | 72.11 / 71.86 | 8.92 / 9.11 | 8.85 / 8.59 |
| 14** | 3-CH₃ | 5-CH₃ | H | CH₂CH₂CH₃ | C₂₅H₃₆N₂O₆ | 133–134 | 65.20 / 64.98 | 7.88 / 8.00 | 6.08 / 5.83 |
| 15* | 2-CH₃ | 3-CH₃ | H | CH₂CH₂CH₃ | C₂₅H₃₆N₂O₆ | 90–91 | 65.20 / 65.19 | 7.88 / 8.03 | 6.08 / 5.99 |
| 16* | 2-CH₃ | 5-CH₃ | H | CH(CH₃)₂ | C₂₅H₃₆N₂O₆ | 87–90 | 62.50 / 64.90 | 7.88 / 7.99 | 6.08 / 5.93 |
| 17** | 3-CH₃ | 5-CH₃ | H | CH(CH₃)₂ | C₂₅H₃₆N₂O₆ | 163–166 | 65.20 / 64.96 | 7.88 / 8.03 | 6.08 / 5.91 |
| 18* | 2-CH₃ | 3-CH₃ | H | CH(CH₃)₂ | C₂₁H₃₂N₂O₂ | oil | 73.21 / 72.92 | 9.36 / 9.61 | 8.13 / 8.04 |
| 19** | 3-CH₃ | 5-CH₃ | H | n-butyl | C₂₆H₃₈N₂O₆ | 118–119 | 65.80 / 65.58 | 8.07 / 8.21 | 5.90 / 5.77 |

*trans form,
*cis form

What is claimed is:

1. The compound of trans-1-(3-Phenylpropyl)-2,5-dimethyl-4-(β-ethoxyacryloyl)piperazine
2. The compound, trans-1-(3-Phenylpropyl)-2,3-dimethyl-4-(β-ethoxyacryloyl)piperazine
3. The compound, trans-1-(3-m-Methylphenyl-propyl)-2,5-dimethyl-4-(β-ethoxyacryloyl)piperazine
4. The compound, trans-1-(3-p-Methylphenylpropyl)-2,5-dimethyl-4-(β-ethoxyacryloyl)piperazine
5. The compound, 1-(3-Phenylpropyl)-3-methyl-4-(β-ethoxyacryloyl)piperazine
6. The compound, cis-1-(3-Phenylpropyl)-3,5-dimethyl-4-(β-ethoxyacryloyl)piperazine
7. The compound, 1-(3-Phenylpropyl)-3-ethyl-4-(β-ethoxyacryloyl)piperazine
8. The compound, 1-(3-p-Methylphenylpropyl)-3-methyl-4-(β-ethoxyacryloyl)piperazine
9. The compounds, trans-1-(3-Phenylpropyl)-2,5-dimethyl-4-(βethoxyacryloyl)piperazine
10. The compound, cis-1-(3-Phenylpropyl)-2,3-dimethyl-4-(β-ethoxyacryloyl)piperazine
11. The compound, cis-1-(3-Phenylpropyl)-3,5-dimethyl-4-(β-methoxyacryloyl)piperazine
12. The compound, trans-1-(3-Phenylpropyl)-2,5-dimethyl-4-(β-methoxyacryloyl)piperazine
13. The compound, trans-1-(3-Phenylpropyl)-2,3-dimethyl-4-(β-methoxyacryloyl)piperazine
14. The compound, cis-1-(3-Phenylpropyl)-3,5-dimethyl-4-(β-n-propoxyacryloyl)piperazine
15. The compound, trans-1-(3-Phenylpropyl)-2,3-dimethyl-4-(β-n-propoxyacryloyl)piperazine
16. The compound, trans-1-(3-Phenylpropyl)-2,5-dimethyl-4-(β-isopropoxyacryloyl)piperazine
17. The compound, cis-1-(3-Phenylpropyl)-3,5-dimethyl-4-(β-isopropoxyacryloyl)piperazine
18. The compound, trans-1-(3-Phenylpropyl)-2,3-dimethyl-4-(β-isopropoxyacryloyl)piperazine
19. The compound, cis-1-(3-Phenylpropyl)-3,5-dimethyl-4-(β-n-butoxyacryloyl)piperazine

* * * * *